United States Patent [19]

Yagi et al.

[11] Patent Number: 4,810,294

[45] Date of Patent: Mar. 7, 1989

[54] SOLUBILIZER FOR WATER-INSOLUBLE ALGINATES, AQUEOUS SOLUTION THEREOF AND DISSOLVING METHOD USING THE AQUEOUS SOLUTION

[75] Inventors: Toshiharu Yagi, Takarazuka; Hiromichi Sakuma; Jouji Saito, both of Settsu, all of Japan

[73] Assignee: Daikin Industries, Ltd., Osaka, Japan

[21] Appl. No.: 138,399

[22] Filed: Dec. 28, 1987

[30] Foreign Application Priority Data

Dec. 29, 1986 [JP] Japan ................................ 61-311325

[51] Int. Cl.$^4$ .............................................. C09K 3/00
[52] U.S. Cl. ...................... 106/35; 106/38.2; 106/38.9; 422/37; 424/52; 424/151; 433/214; 252/106
[58] Field of Search .............. 106/38.2, 38.22, 38.9, 106/35; 422/37; 424/52, 151, 166; 252/106; 433/214

[56] References Cited

U.S. PATENT DOCUMENTS 4,515,913  5/1985  Pellico ................................ 106/35

OTHER PUBLICATIONS

The Merck Index, Eighth Edition, 1968, pp. 68, 854, 959.

Primary Examiner—Paul Lieberman
Assistant Examiner—Helene Kirschner
Attorney, Agent, or Firm—Armstrong, Nikaido, Marmelstein & Kubovcik

[57] ABSTRACT

A solubilizer for water-insoluble aliginates consisting essentially of a salt which releases fluorine ions when dissolved in water, an aqueous solution of the solubilizer and a dissolving method with use of the aqueous solution are described.

13 Claims, No Drawings

SOLUBILIZER FOR WATER-INSOLUBLE ALGINATES, AQUEOUS SOLUTION THEREOF AND DISSOLVING METHOD USING THE AQUEOUS SOLUTION

The present invention relates to a solubilizer for water-insoluble alginates, an aqueous solution thereof and a dissolving method using the aqueous solution.

Alginic acid is a kind of organic high-molecular-weight substance in the form of a hydrophilic colloid and prepared from seaweeds or marine plants by a complex chemical process and purification. While the acid finds various uses, water-insoluble salts thereof are utilized in connection with surgical gauze, sutures, dental impression materials, water softeners, clarifiers, etc. More specifically, sodium alginate is spinned into yarns, water-insolubilized, and made into surgical gauze or used as sutures or the like. Sodium alginate, incorporated in a dental impression material, changes into calcium alginate on reaction with calcium sulfate when used and is thereby rendered insoluble in water to form an impression. Sodium alginate, when serving as a component of a water softener or clarifier, undergoes ion exchange with iron, calcium and the like ions in hard water or in an aqueous suspension and precipitates in the form of water-insoluble salts such as iron alginate and calcium alginate, softening the water or clarifying the suspension.

The use of alginic acid encounters a problem as will be described below, for example, with reference to the dental impression material. The dental impression material is used for preparing impressions of internal portions of the oral cavity to remedy defective teeth such as decayed teeth. The utensil for holding the impression material is called an impression tray. A tooth model is prepared by forming an imprint with the material and placing gypsum into the impression obtained on gelation of the imprint. When the gelled impression is thereafter removed from the tray to use the tray repeatedly, the gelled impression material remaining on the tray must be removed using a tray cleaner.

The conventional tray cleaners include sodium polyphosphate, sodium carbonate, etc. These cleaners require much time for removing the gelled impression material, are not very effective for decomposing the material and therefore need a cumbersome procedure such as washing the tray with pressurized water in addition to the application of the cleaner, or forcibly rubbing the tray as with a brush to remove the remaining material.

It appears possible to remove, for example, such adhering gelled impression material easily from the impression tray if a solubilizer is developed for dissolving water-insoluble alginates resulting from the use of various materials or agents like those mentioned above. Furthermore, the suture used for surgery can be dissolved, or the water softener or clarifier once used can be regenerated, using the solubilizer.

An object of the present invention is to provide a solubilizer which is highly soluble in water for dissolving water-insoluble alginates.

Another object of the invention is to provide an aqueous solution of solubilizer which is neutral and assures high safety for dissolving water-insoluble alginates.

The above and other objects of the invention will become apparent from the following description.

The present invention provides a solubilizer for water-insoluble alginates consisting essentially of a salt which releases fluorine ions when dissolved in water, an aqueous solution of the solubilizer and a dissolving method with use of the aqueous solution.

According to the invention, examples of suitable salts which release fluorine ions when dissolved in water are sodium fluoride, potassium fluoride, ammonium fluoride and the like.

According to the invention, examples of water-insoluble alginates are alginic acid salts of metals generally having a valence of at least two, such as calcium, barium, aluminum, zinc, copper, silver, iron, lead and the like.

The solubilizer of the invention is used in the form of an aqueous solution. The concentration of the salt which releases fluorine ions when dissolved in water is preferably about 0.01 to about 10wt. %, more preferably about 0.1 to about 4wt. %.

The aqueous solution of the present solubilizer is substantially neutral in pH and need not contain any pH adjusting agent. If the hand is exposed directly to the present solubilizer, the solubilizer does not roughen the skin. Further, even if it enters the eye, the solubilizer is not very hazardous, hence it has high safety.

When used, for example, as a tray cleaner, the solubilizer solution of the invention may have incorporated therein desired additives which will not impair its effect, such as sodium sulfate, sodium silicate and like auxiliary agents, penetrants, pigments, etc. The solubilizer is further usable in combination with conventional tray cleaners such as sodium polyphosphate, sodium carbonate and sodium citrate.

The gelled impression material remaining on impression trays is removable with the aqueous solubilizer solution of the invention, for example, by immersing the tray in the solution after removing the mass of material (impression), occasionally shaking the solution when desired and thereafter washing the tray with water.

The solubilizer of the invention is usable for various purposes, for example, as a cleaner for dental impression trays, an agent for dissolving surgical gauze and sutures, a regenerating agent for used water softeners and clarifiers, etc. The solubilizer is also usable, for example, for cleaning impression trays used for making patterns for molds in metal casting and plastic molding.

The solubilizer of the invention dissolves water-insoluble alginates rapidly in large amounts.

The present solubilizer dissolves in water at room temperature, exhibits a sufficient effect at a low concentration of about 2% and is therefore economical.

Furthermore, the present aqueous solution of solubilizer is substantially neutral in pH and antiseptic.

The invention will be described in greater detail with reference to the following examples, in which percentages are by weight.

EXAMPLE 1

Denta Lieben (product of Daikin Industries, Ltd.) serving as an alginate impression material was kneaded with water in a specified ratio and made into a gelled test piece in the form of a solid cylinder, 13 mm in diameter and 20 mm in height.

The test piece was placed on a 20-mesh metal net and immersed in 2% aqueous solution of sodium fluoride. The piece completely dissolved in 3 hours.

EXAMPLE 2

The same procedure as in Example 1 was repeated with the exception of using Algiace New Mix (product of SANKIN Industry Co., Ltd.) instead of Denta Lieben. The test piece completely dissolved in 5 hours.

EXAMPLE 3

The same procedure as in Example 1 was repeated with the exception of using Algino plast (product of Bayer A.G., West Germany) instead of Denta Lieben. The test piece completely dissolved in 5 hours.

EXAMPLE 4

The same procedure as in Example 1 was repeated with the exception of using 0.5%, 1% or 2% aqueous solution of potassium fluoride. The test piece in each solution dissolved completely in 5 hours.

EXAMPLE 5

The same procedure as in Example 1 was repeated with the exception of using 2% aqueous solution of ammonium fluoride. The test piece completely dissolved in 3.5 hours.

EXAMPLE 6

The same procedure as in Example 1 was repeated with the exception of using a mixture of 2% aqueous solution of sodium fluoride and 2% aqueous solution of potassium fluoride in equal volumes. The test piece completely dissolved in 3 hours.

EXAMPLE 7

The same procedure as in Example 1 was repeated with the exception of using a mixture of 2% aqueous solution of sodium fluoride and 2% aqueous solution of sodium carbonate in equal volumes. The test piece completely dissolved in 5 hours.

COMPARATIVE EXAMPLE 1

The same procedure as in Example 1 was repeated with the exception of using 3.6% aqueous solution of sodium polyphosphate, but the test piece did not dissolve completely even in 24 hours. The remaining portion of the test piece was removable by washing with pressurized water.

COMPARATIVE EXAMPLE 2

The same procedure as in Example 1 was repeated with the exception of using 4% aqueous solution of sodium carbonate, but the test piece did not dissolve completely even in 24 hours. The remaining portion of the test piece was completely removable by forcible brushing.

COMPARATIVE EXAMPLE 3

The same procedure as in Comparative Example 1 was repeated with the exception of using 2% aqueous solution of sodium citrate in place of 3.6% sodium polyphosphate solution. The same result as in Comparative Example 1 was achieved.

COMPARATIVE EXAMPLES 4 AND 5

The same procedure as in Comparative Example 1 was repeated with the exception of using 2% aqueous solution of trisodium ethylenediaminetetraacetate or tetrasodium ethylenediaminetetraacetate instead of 3.6% sodium polyphosphate solution. The same result as in Comparative Example 1 was achieved by each solution.

We claim:

1. An aqueous solution of a solubilized alginate, comprising:
   a water-insoluble alginate;
   a solubilizing amount of a salt releasing fluoride ions when dissolved in water; and
   water.

2. An aqueous solution according to claim 1, wherein the salt releasing fluoride ions is one selected from the group of sodium fluoride, potassium fluoride and ammonium fluoride.

3. An aqueous solution according to claim 1, wherein the water-insoluble alginate is an alginic acid salt of a metal selected from the group consisting of calcium, barium, aluminum, zinc, copper, silver, iron and lead.

4. An aqueous solution according to claim 1, wherein the concentration of salt which releases fluoride ions in water is about 0.01 to about 10 wt. %.

5. A combination comprising a water-insoluble alginate, water, and a salt releasing fluoride ions when dissolved in water, said salt being present in an amount sufficient to solubilize said alginate.

6. A combination according to claim 5, wherein the salt releasing fluoride ions is one selected from the group consisting of sodium fluoride, potassium fluoride and ammonium fluoride.

7. A combination according to claim 5, wherein the water-insoluble alginate is an alginic acid salt of a metal selected from the group consisting of calcium, barium, aluminum, zinc, copper, silver, iron and lead.

8. A combination according to claim 5, wherein the concentration of salt which releases fluoride ions in water is about 0.01 to about 10 wt. %.

9. A method of solubilizing a water-insoluble alginate, comprising the step of:
   contacting said water-insoluble alginate with an aqueous solution containing a solubilizing amount of a salt releasing fluoride ions.

10. A method according to claim 9, wherein the salt releasing fluoride ions is one selected from the group consisting of sodium fluoride, potassium fluoride and ammonium fluoride.

11. A method according to claim 9, wherein the water-insoluble alginate is an alginic acid salt of a metal selected from the group of calcium, barium, aluminum, zinc, copper, silver, iron and lead.

12. A method according to claim 9, wherein the concentration of salt which releases fluoride ions in water is about 0.01 to about 10 wt. %.

13. A method according to claim 9, wherein said water-insoluble alginate is immersed in said aqueous solution, and then washed with water.

* * * * *